(12) United States Patent
Noonan et al.

(10) Patent No.: US 7,680,958 B2
(45) Date of Patent: Mar. 16, 2010

(54) ADAPTIVE TRANSACTION MESSAGE FORMAT DISPLAY INTERFACE FOR USE IN A MESSAGE DATA EXCHANGE SYSTEM

(75) Inventors: Julianne Noonan, Boyertown, PA (US); Maryann Feng, Exton, PA (US); Richard J. Gengler, West Chester, PA (US); Mark J. Noonan, Boyertown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 340 days.

(21) Appl. No.: 11/765,038

(22) Filed: Jun. 19, 2007

(65) Prior Publication Data

US 2008/0016244 A1 Jan. 17, 2008

Related U.S. Application Data

(60) Provisional application No. 60/807,099, filed on Jul. 12, 2006, provisional application No. 60/891,567, filed on Feb. 26, 2007.

(51) Int. Cl.
*G06F 15/16* (2006.01)
*G06F 15/173* (2006.01)

(52) U.S. Cl. .................. 709/246; 709/238; 709/245

(58) Field of Classification Search .................. 709/246, 709/238
See application file for complete search history.

(56) References Cited

U.S. PATENT DOCUMENTS 4,455,624 A 6/1984 Haag et al.
6,189,140 B1 2/2001 Madduri
6,415,341 B1* 7/2002 Fry et al. .................... 710/62
7,233,595 B1* 6/2007 Hollis et al. ............. 370/395.2
2002/0035560 A1* 3/2002 Sone ............................. 707/5
2004/0006608 A1* 1/2004 Swarna et al. .............. 709/220
2004/0010773 A1* 1/2004 Chan et al. .................. 717/104
2005/0114391 A1* 5/2005 Corcoran et al. ........ 707/103 R
2005/0141472 A1* 6/2005 Shin et al. ................... 370/342
2008/0133577 A1* 6/2008 Noonan et al. ............. 707/102

* cited by examiner

*Primary Examiner*—Wing F Chan
*Assistant Examiner*—Razu A Miah
(74) *Attorney, Agent, or Firm*—Alexander J. Burke (57) ABSTRACT

A system provides an integration engine debugging and trace function that adaptively captures and displays trace information and promotes easier and more efficient troubleshooting. A system adaptively displays transaction message data for use with a data exchange system for exchanging data between different computer systems using different data formats. The system includes a repository of data comprising transaction messages communicated between different computer systems using different data formats. A data converter converts transaction message data into Hex and non-Hex representations. A display processor provides data representing a first display image including data representing a single transaction message in both Hex and non-Hex data format and enabling a user to initiate generation of a second display image for presenting the transaction message exclusively in a non-Hex representation.

17 Claims, 10 Drawing Sheets

ADAPTIVE TRANSACTION MESSAGE FORMAT DISPLAY INTERFACE FOR USE IN A MESSAGE DATA EXCHANGE SYSTEM

This is a non-provisional application of provisional application Ser. No. 60/807,099 by J. Noonan et al. filed Jul. 12, 2006 and of provisional application Ser. No. 60/891,567 by J. Noonan et al. filed Feb. 26, 2007.

FIELD OF THE INVENTION

This invention concerns a system for adaptively displaying transaction message data for use with an integration engine exchanging data between different computer systems using different data formats.

BACKGROUND OF THE INVENTION

Known systems monitor communication of messages in an integration engine (a system for exchanging data between different computer systems using different data formats) using trace data. The trace data typically contains either a view of message data in a Hex representation or a view of the data in a non-Hex (e.g., an ASCII) representation without providing a user with an option to select the type of representation for display. Additionally, in known integration engines, a trace function is typically turned on and off via a command line interaction. A user desires to look at trace data without Hex characters (non-Hex trace data) currently included in trace data as an easy to read representation of message data being communicated by an integration engine. The non-Hex trace data is also used to facilitate troubleshooting and may be provided to message source or destination entities for review. Conversely, support personnel use a Hex trace data representation of message data being transmitted for troubleshooting and debugging purposes.

In known systems, both Hex and textual (e.g., ASCII) representations of message data being transmitted are typically included in the same file and in order to produce a desired output it is necessary to manually copy individual portions of trace data and paste the individual pieces back together. Also known systems typically require user command line intervention to debug program or trace execution steps. Further known systems require a user to manipulate command line programming to gather data and decide prior to initiating a trace function how message trace data is to be represented (if there is a choice). Known systems further provide only one view of traced message data that is traced and do not have the flexibility to readily present the same data in different views. Alternatively known systems only provide a view of message trace data in a format that includes both Hex and non-Hex format data. A system according to invention principles addresses these deficiencies and related problems.

SUMMARY OF THE INVENTION

A system provides an integration engine debugging and trace function that adaptively captures and displays trace information, via a Graphical User Interface (GIU), in either Hexadecimal (Hex), binary (e.g., for DICOM, HL7 transactions and image representation) or character (e.g., ASCII) representations enabling a user to toggle between alternate representations of the data. A system adaptively displays transaction message data for use with a data exchange system for exchanging data between different computer systems using different data formats. The system includes a repository of data comprising transaction messages communicated between different computer systems using different data formats. A data converter converts transaction message data into Hex and non-Hex representations. A display processor provides data representing a first display image including data representing a single transaction message in both Hex and non-Hex data format and enabling a user to initiate generation of a second display image for presenting the transaction message exclusively in a non-Hex representation.

DETAILED DESCRIPTION OF THE INVENTION

A system adaptively displays transaction message data for use with an integration engine debugging and trace function that enables a user to view message trace information, via a Graphical User Interface (GUI), in either Hexadecimal (Hex) or character (ASCII) or Binary representations. An integration engine is a system for exchanging data between different computer systems using different incompatible data formats. The GUI enables flexibility in capture of the trace data and enables a user to toggle between alternate representations of the data. This enables different users of an integration engine who have different requirements for receiving information and format of received information, to dynamically identify data to be collected as well as the format in which the collected data is to be represented. The GUI trace function enables a user to dynamically toggle between image views with and without Hex representation of data. Specifically, the system supports dynamic toggling between the Hex representation with text data, Hex representation without text data, text data without Hex representation and a binary view of data via a graphical user interface.

The system automatically generates message trace data and provides a user with multiple views of the data (e.g., including one or more of binary, character or Hex representation of message data) without the need for a source of a message to retransmit the message with particular integration engine processing operations, e.g., selected by setting particular message data indicators. This advantageously reduces time involved in troubleshooting a message transaction performed by an integration engine. A user is also able to establish a configuration preference indicating a default display data format representation and view for presenting data upon initiating access to the system. A view preference is maintained for each individual user thereby eliminating a need for a user to repetitively select a preferred view. A default display data format representation may comprise one or more of, binary, character or Hex representation of message data. The system advantageously provides an adaptive view of message data facilitating faster more efficient troubleshooting and associated problem solving concerning message data processing.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of hardware, firmware, and/or software.

An executable application, as used herein, comprises code or machine readable instructions for conditioning the processor to implement predetermined functions, such as those of an operating system a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by a display processor enabling user interaction with a processor or other device and associated data acquisition and processing functions. The UI also includes an executable procedure or executable application. The executable procedure executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of the executable procedure or executable application manipulates the UI display images in response to the signals received from the input devices. In this way, the user interacts with the display image using the input devices, enabling user interaction with a processor or other device. The activities herein may be performed automatically or wholly or partially in response to user command. An automatically performed activity is performed in response to machine instruction or operation without direct user interaction in initiating the activity. Further Hex format also includes Octal format.

Figure 1:
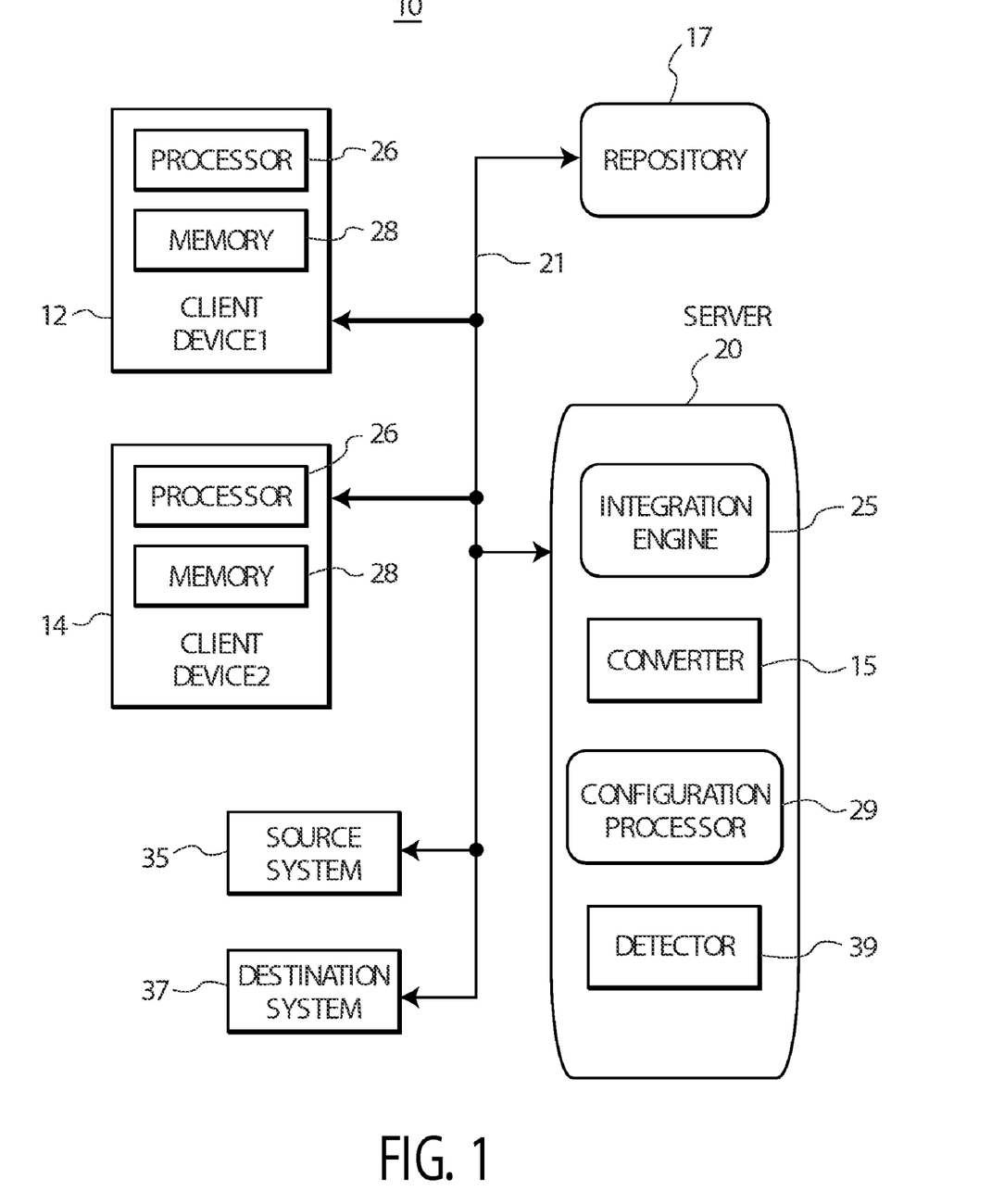
FIG. 1 shows a system for adaptively displaying transaction message data for use with a data exchange system for exchanging data between different computer systems using different data formats, according to invention principles.

FIG. 1 shows adaptive transaction message data display system 10 for use with a data exchange system (integration engine 25) for exchanging data between different computer systems using different data formats. Message data display system 10 includes client devices (workstations) 12 and 14, repository 17 and server 20 including integration engine 25, converter 15, configuration processor 29 and detector 39 that bidirectionally communicate via network 21. Interface engine 25 processes and converts transaction message data from source system 35 to be compatible with destination system 37 and communicates the converted transaction message data to system 37. Repository 17 includes data comprising transaction messages communicated between different computer systems 35 and 37 using different data formats. Data converter 15 converts transaction message data into Hex and non-Hex (e.g., Binary and character (text) representations). Display processor 26 in workstation 12 (and in workstation 14) or in another embodiment in server 20, provides data representing a first display image including data representing a single transaction message in both Hex and non-Hex data format and enabling a user to initiate generation of a second display image for presenting the transaction message exclusively in a non-Hex representation.

Figure 5:
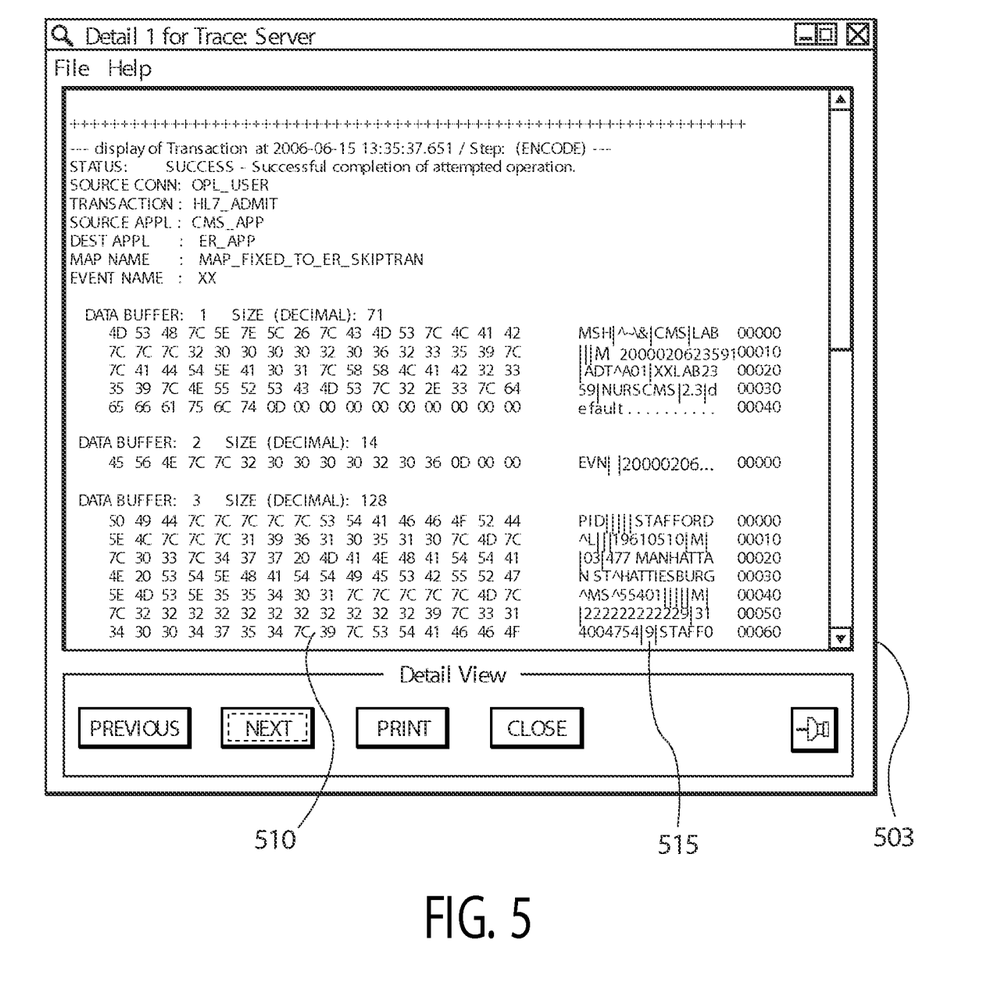
FIG. 5 shows a user interface display image illustrating message data in Hex and ASCII representations without an option to remove the Hex representation, according to invention principles.

Configuration processor 29 enables a user to enter data determining a user preference for display of transaction message data exclusively as at least one of, (a) a Hex representation, (b) a non-Hex representation, (c) a binary representation and (d) an image representation. Detector 39 automatically detects a transaction message type in response to metadata associated with a message and display processor 26 automatically adaptively provides data representing a display image including data representing a single transaction message exclusively in a selected one of Hex, non-Hex and an image representation data format in response to the metadata. FIG. 5 shows user interface display image 503 illustrating message data in Hex 510 and (non-Hex) ASCII 515 representation without an option to remove the Hex representation.

Figure 2:
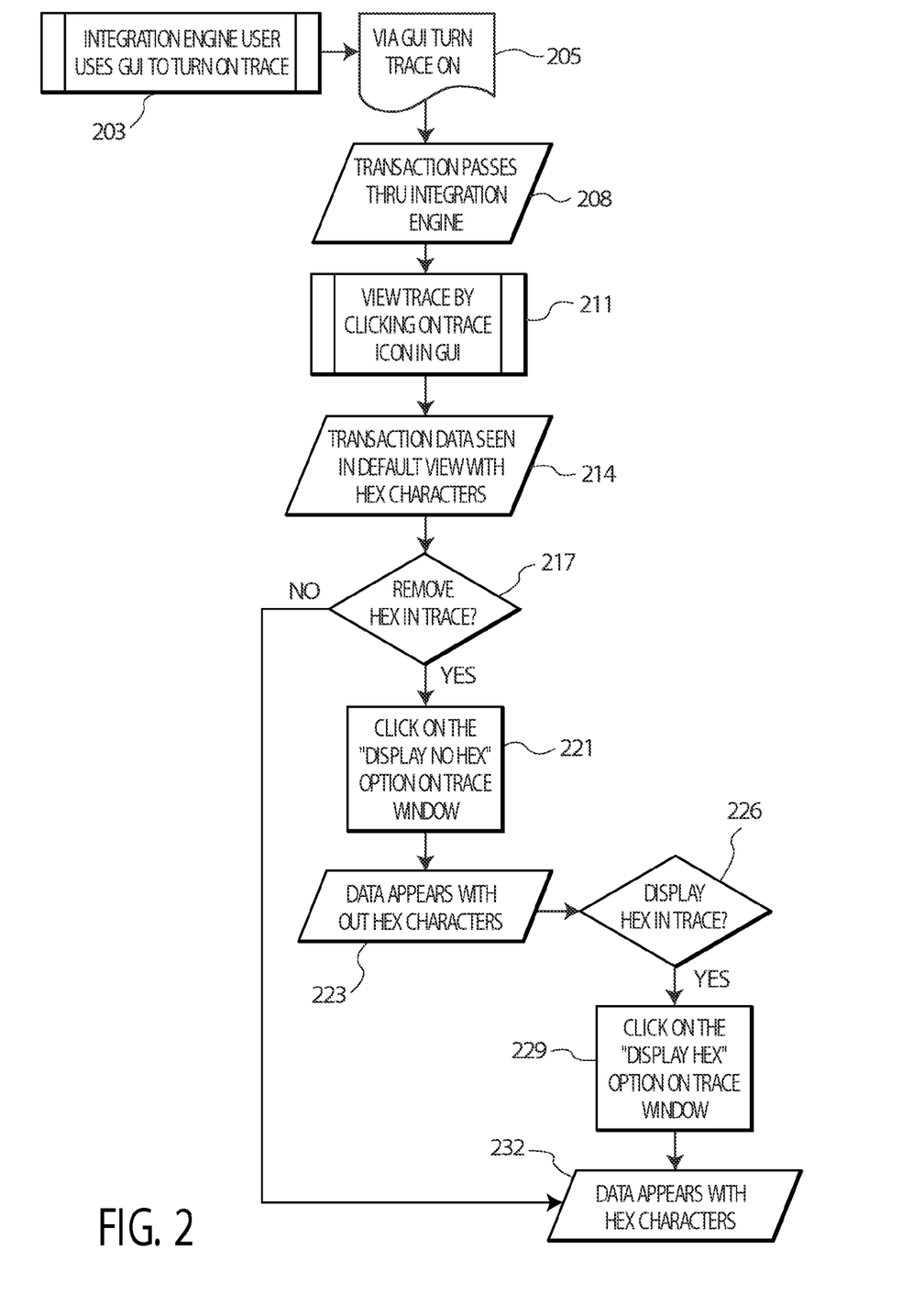
FIG. 2 shows a flowchart of a process for switching between Hex and non-Hex message data representations employed by a system for adaptively displaying transaction message data, according to invention principles.
Figure 6:
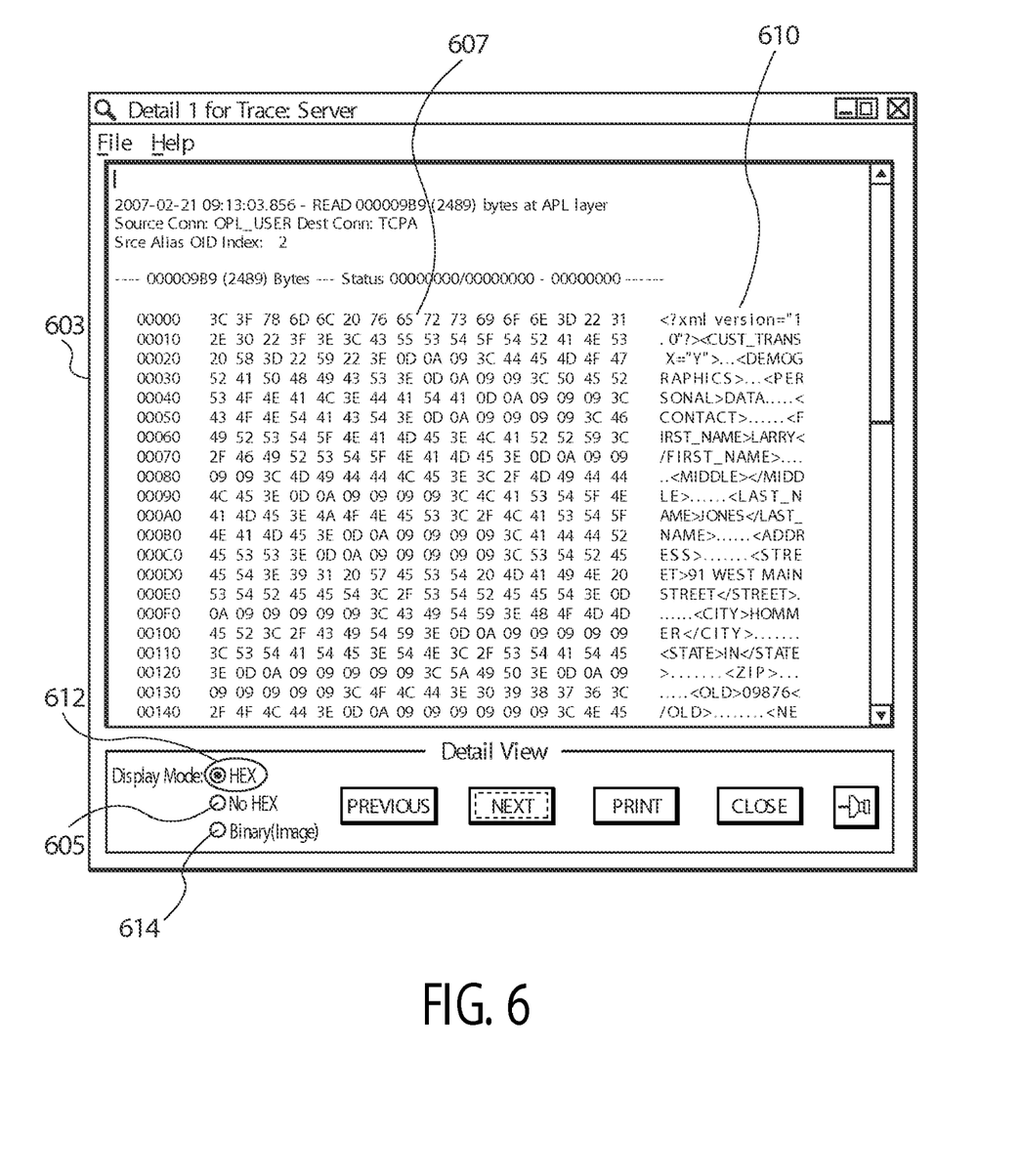
FIG. 6 shows a user interface display image illustrating message data in Hex and ASCII representations with an option to remove the Hex representation, according to invention principles.

FIG. 2 shows a flowchart of a process for switching between Hex and non-Hex message data representations employed by system 10 (FIG. 1) for adaptively displaying transaction message data. In operation, destination system 37 indicates that message data received from source system 35 via integration engine 25 is in error. A user needs to determine what message data was sent by system 35 and in what format and desires to see the various non-viewable control characters including carriage returns and line feeds in the message data that is not viewable in a textual representation of the data. A user in steps 203 and 205 initiates activation of a message data trace function in integration engine 25 via a user interface displayed on workstation 12. In step 208, message data is communicated from source system 35 via integration engine 25 to destination system 37 and a user in step 211 selects a button in a message trace user interface image displayed on workstation 12 to access and view the communicated message data. In step 214 the message data is presented to a user via workstation 12 in a default image view in Hex format. FIG. 6 shows user interface display image 603 illustrating message data in Hex 607 and ASCII 610 representations provided in step 214 (FIG. 2) together with option 605 enabling a user to initiate removal of the Hex representation.

Figure 7:
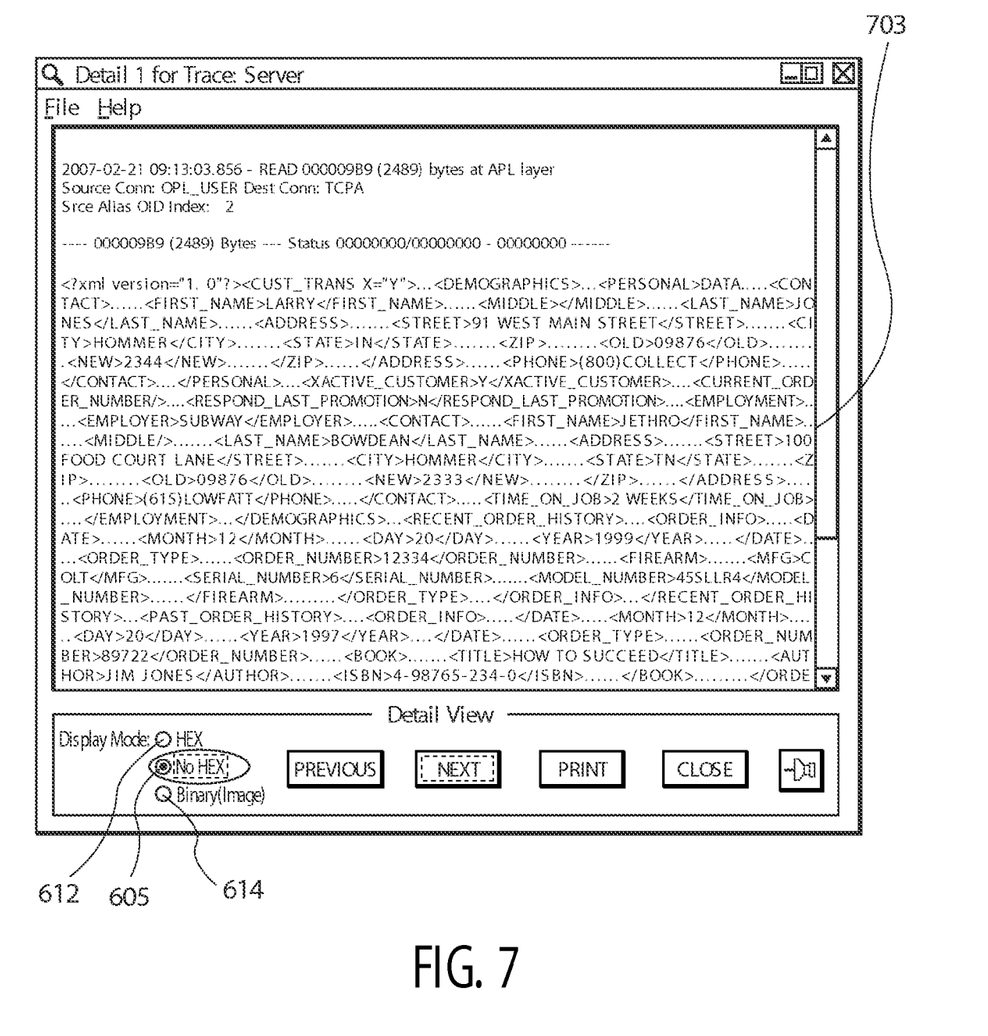
FIG. 7 shows a user interface display image illustrating message data in ASCII representation with the Hex representation removed, according to invention principles.

In step 217, in response to a user determining not to remove the Hex format data representation, the message data is presented with Hex format data in step 232. In step 217, in response to a user determining to remove the Hex data representation and selecting option 605 (FIG. 6) in step 221, the message data is presented in exclusively non-Hex format in step 223. FIG. 7 shows use interface display image 703 illustrating message data in ASCII representation with the Hex representation removed as indicated in option 605. A user is able to toggle between Hex and non-Hex views of the message via options 605, 612 and 614. For example, in step 226, in response to a user determining to again display a Hex data representation and selecting option 612 (FIG. 7) in step 229, the message data is presented with Hex format data in step 232.

Figure 3:
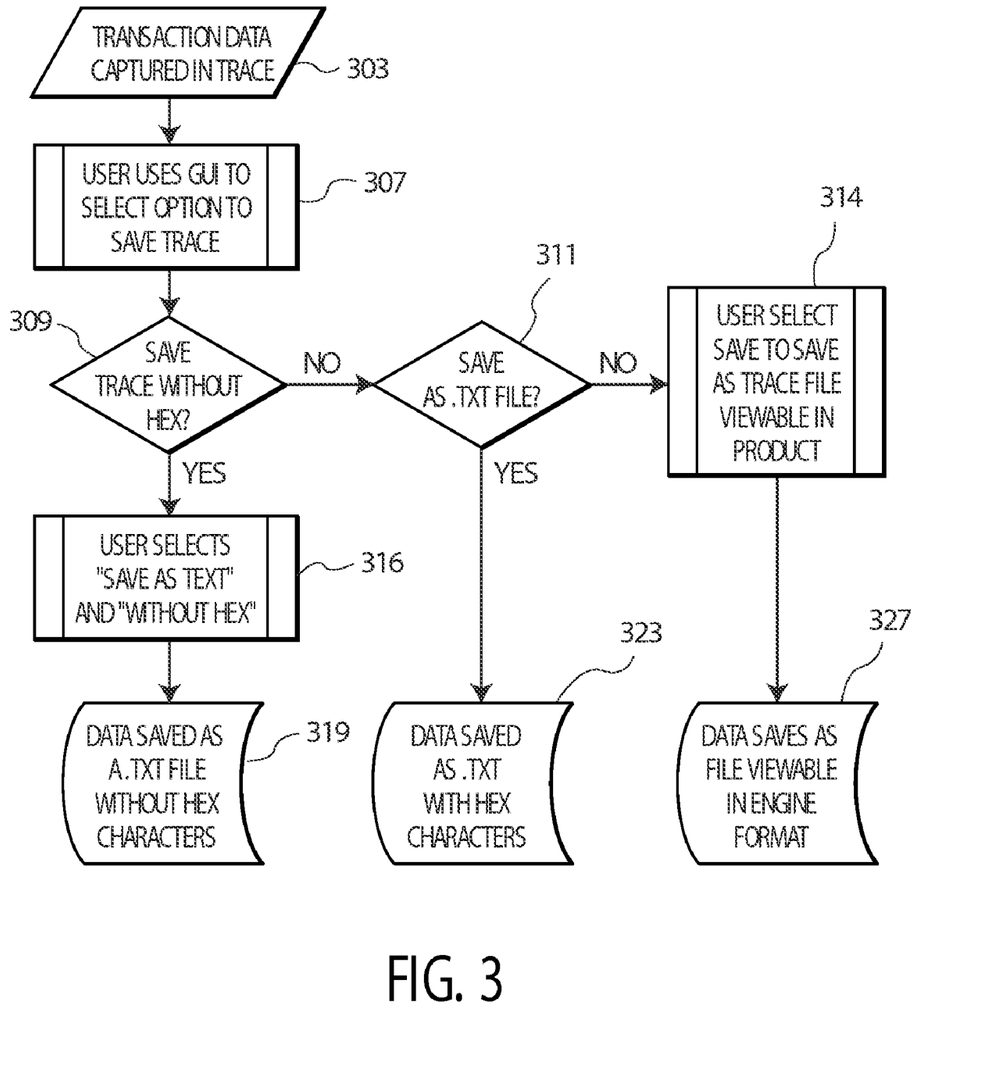
FIG. 3 shows a flowchart of a process for saving non-Hex trace message data employed by a system for adaptively displaying transaction message data, according to invention principles.
Figure 9:
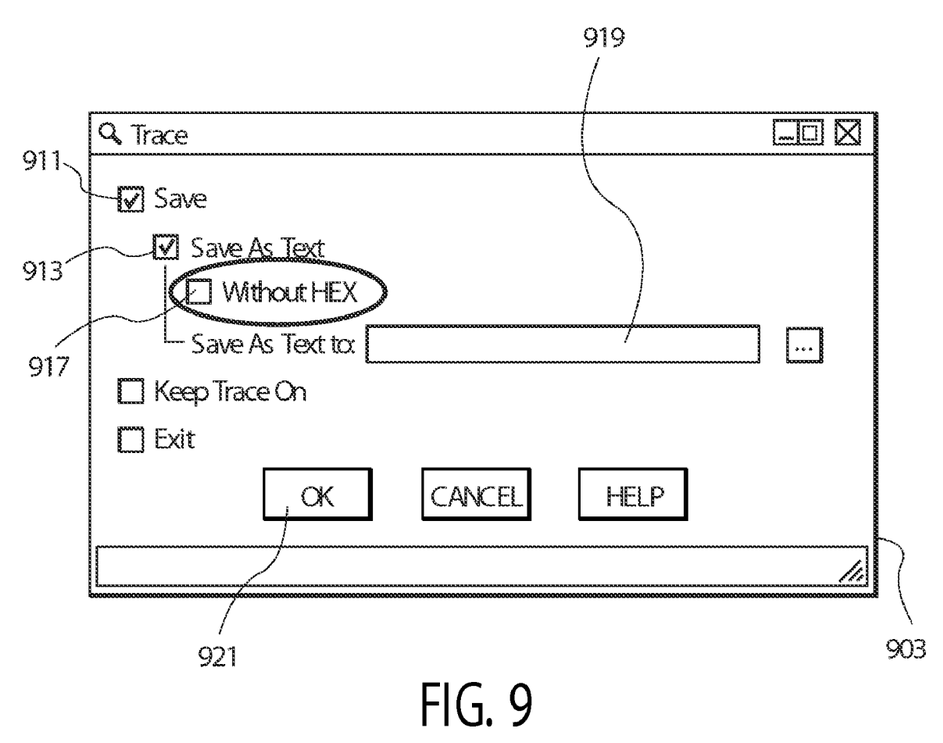
FIG. 9 shows a user interface display image menu enabling a user to save trace message data with or without Hex representation data, according to invention principles.

FIG. 3 shows a flowchart of a process employed by system 10 for saving trace message data without Hex data. In step 303 trace message data is captured. A user views the trace message data together with a Hex representation of the data (in order to enable a user see non-printable control characters) in a UI display image presented on workstation 12. The user verifies that carriage returns and line feeds are correct and desires to provide a file with just the message data for troubleshooting. The user uses a toggle button (e.g., button 605 FIG. 6) to view the trace message data without Hex. There is no need to wait for additional records to pass through integration engine 25 or to be resent through integration engine 25 with an alternate configuration because the Hex data is still in memory but is hidden from view. The user in step 307 selects UI option 911 in the FIG. 9 user interface display image menu 903 presented on workstation 12 in response to user command to save the trace message data.

In step 309 the user decides whether to save the message data with or without Hex data. In response to determining to save the message data with Hex data the user determines whether to save the message as text in step 311, and if so selects a save to text file option 913 (FIG. 9) and indicates where to save the text together with a corresponding Hex format data representation using box 919. The message data is saved in response to user selection of button 921. If the user determines not to save the message data as text in step 311 and elects to save the message data in step 314, the message data is saved in a data format provided by integration engine 25 in step 327 in response to user selection of button 921. In response to determining to save the message data without Hex data in step 309, the user in step 316 selects save to text file option 913 (FIG. 9) and without Hex option 917. The message data is saved as a text file without Hex in step 319 in response to user selection of button 921. Further, in response to a user turning off a trace function, system 10 saves message data with Hex format data by default. However, FIG. 9 enables a user to save message data to a text file without including corresponding Hex format data. Also a user is able to use a text file in any way desired including by viewing it outside of integration engine 25.

Figure 4:
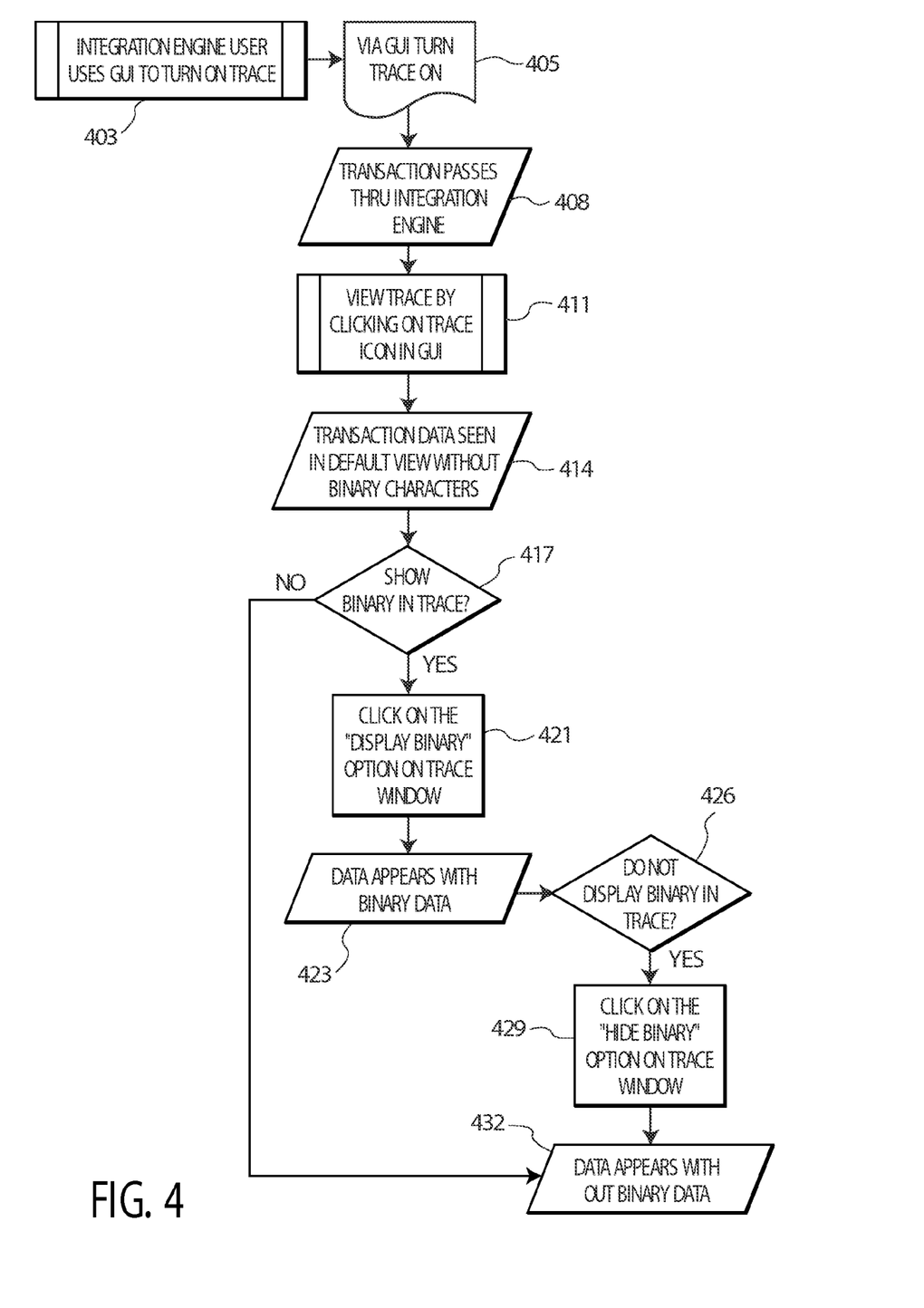
FIG. 4 shows a flowchart of a process for switching between Binary and non-Binary message data representations employed by a system for adaptively displaying transaction message data, according to invention principles.

FIG. 4 shows a flowchart of a process for switching between Binary and non-Binary message data representations employed by system to (FIG. 1) for adaptively displaying transaction message data. In operation, destination system 37 indicates that DICOM or other Binary message data received from source system 35 via integration engine 25 is in error. A user needs to determine what message data was sent by system 35 and in what format and desires to see the various non-viewable control characters, including carriage returns and line feeds in the message data that is not viewable in a textual representation of the data. A user in steps 403 and 405 initiates activation of a message data trace function in integration engine 25 via a user interface displayed on workstation 124. In step 408, message data is communicated from source system 35 via integration engine 25 to destination system 37 and a user in step 411 selects a button in a message trace user interface image to access and view the communicated message data together with a Binary representation of the data. In step 414 the message data is presented to a user via workstation 12 in a default image view without Binary data.

Figure 8:
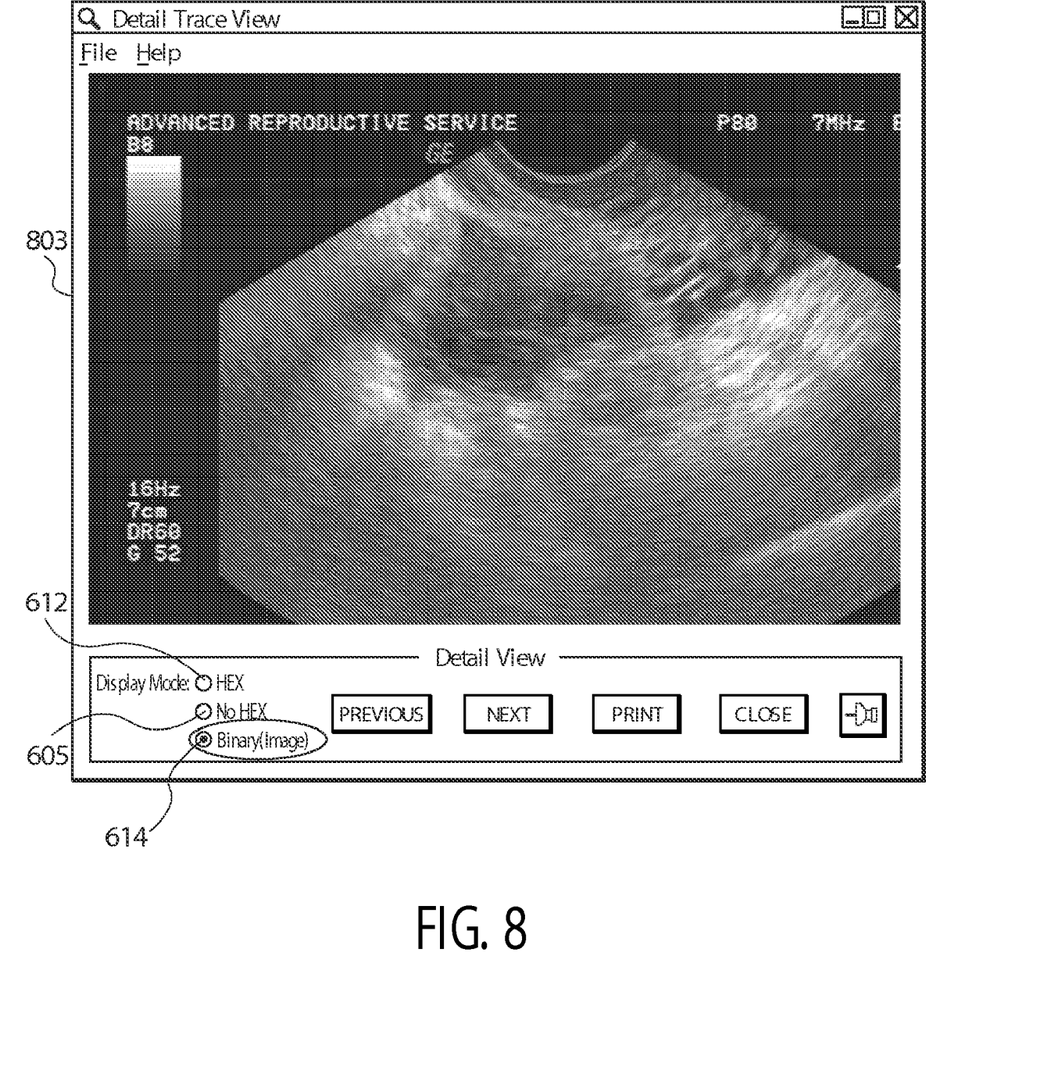
FIG. 8 shows a user interface display image illustrating medical image message data in Binary representation, according to invention principles.

In step 417, in response to a user determining not to view a Binary format data representation, the message data is presented without Binary format data in step 432. In step 417, in response to a user determining to view a Binary format data representation and selection of an associated button option 614 (FIG. 6) in step 421, the message data is presented in a Binary format representation in step 423. FIG. 8 shows user interface display image 803 (an ultrasound image) illustrating medical image message data in Binary representation. A user is able to toggle between Binary and non-Binary views of the message via options 605, 612 and 614. For example, in step 426, in response to a user determining to remove the Binary data representation and de-selecting option 614 (FIG. 8) in step 429, the message data is presented without Binary format data in step 432.

System 10 incorporates functions to include or not include Hex or Binary data in a display of message data without a user needing to know programming commands. System 10 enables a user to toggle between views of data with Hex and without Flex and Binary and allows a user to troubleshoot in various ways without having to reconfigure message trace options and resend message data. System 10 supports sharing, message data for troubleshooting purposes without Hex characters enabling, faster more efficient troubleshooting. For example, when troubleshooting a clinical (e.g. laboratory test) result message transaction, it is desired to see the data in the trace without the Hex turned on. It may typically take a minimum of ten minutes, for example, to manually copy and paste an individual line of the message transaction without copying the Hex data representation of the individual line. Additional time is required for copying data such as DICOM images that typically arc in Binary format. System 10 functions enable a user to view the data either with or without the Binary data depending on the view that is desired in a particular circumstance. System 10 acquires both message data and corresponding Hex format representation data for a message during a trace operation and allows a user to toggle between views.

Figure 10:
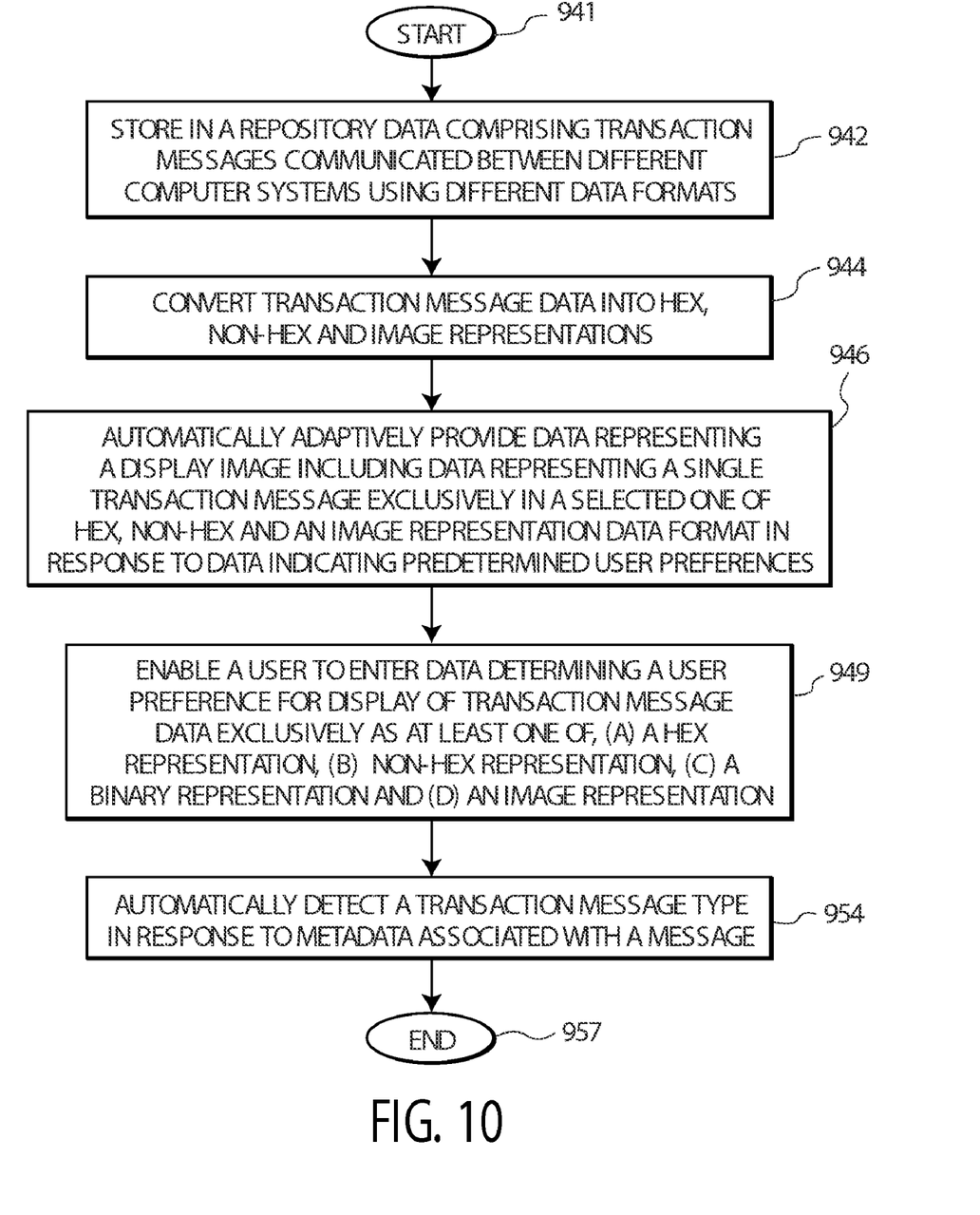
FIG. 10 shows a flowchart of a process performed by a system for adaptively displaying transaction message data, according to invention principles.

FIG. 10 shows a flowchart of a process performed by system 10 (FIG. 1) for adaptively displaying transaction message data. In step 942 following the start at step 941, data comprising transaction messages communicated between different computer systems using different data formats is stored in repository 17 (FIG. 1). In step 944 converter 15 converts transaction message data into Hex, non-Hex (e.g., text, ASCII dataset compatible) and image (e.g., binary comprising, JPEG, mpeg etc.) representations. The non-Hex representation also may comprise an image representation format. Display processor 26 in step 946 automatically adaptively provides data representing a display image including data representing a first display image including a single transaction message exclusively in a selected one of Hex, non-Hex and an image representation data format in response to at least one of, user selection of a displayed image element, data indicating predetermined user preferences and metadata associated with a message. Display processor 26 enables a user to initiate generation of a second display image for presenting the transaction message exclusively in a non-Hex or image representation data format. The second display image comprises an image window in the first display image or overlaying data in the first display image. The first display image may also comprise data representing a single transaction message in both Hex and non-Hex data format and enable a user to initiate generation of a second display image for presenting the transaction message exclusively in an image representation format.

In step 949 configuration processor 29 enables a user to enter data determining a user preference for display of transaction message data exclusively as at least one of, (a) a Hex representation, (b) a non-Hex representation, (c) a binary representation and (d) an image representation. Configuration processor 29 enables a user to enter data determining user preferences for display of different types of transaction message data in corresponding different types of data representations. A detector in step 954 automatically detects a transaction message type in response to metadata associated with a message. The process of FIG. 10 terminates at step 957.

The system, processes and image displays of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 is not limited to be used only for health care information systems. The system is of advantage for any application of an integration engine in any field and may be used to reduce the need for special network traces and "network sniffer" traces. A user may need to see both message data and a Hex representation of the data for troubleshooting message data transfer through an integration engine. For this purpose a user may need to see the data without the Hex or Binary data and copy and paste it into some other document for collaborative problem solving. The processes and applications provided by system 10 (FIG. 1) may in alternative embodiments, be located on one or more (e.g., distributed) processing devices accessing a network linking the FIG. 1 elements or that are remotely accessible. Further, any of the functions and steps provided in FIGS. 1-10 may be implemented in hardware, software or a combination of both.

What is claimed is:

1. A system for adaptively displaying transaction message data for use with a data exchange system used for exchanging data between different computer systems using different data formats, comprising:
   a repository of data comprising transaction messages communicated between different computer systems using different data formats;
   a configuration processor enabling a user to enter data determining user preferences for display of different types of transaction message data in corresponding different types of data representations;
   a data converter for converting transaction message data derived from the repository into Hex and non-Hex representations;
   a detector for automatically detecting a transaction message type in response to metadata associated with a message; and
   a display processor for providing data representing a first display image including data representing a single transaction message in both Hex and non-Hex data format and enabling a user to initiate generation of a second display image for presenting said transaction message exclusively in a non-Hex representation, said display processor automatically adaptively provides data representing a display image including data representing a single transaction message in a selected one of Hex, non-Hex and an image representation data format in response to said metadata.

2. The system according to claim 1, wherein said non-Hex representation is an ASCII dataset compatible representation.

3. The system according to claim 1, wherein said second display image comprises an image window overlaying data in said first display image.

4. The system according to claim 1, wherein said second display image comprises an image window in said first display image.

5. The system according to claim 1, wherein said data converter converts transaction message data into a binary representation.

6. The system according to claim 1, wherein said data converter converts transaction message data into an image representation and
   said display processor for providing data representing a first display image including data representing a single transaction message in both Hex and non-Hex data format and enables a user to initiate generation of a second display image for presenting said transaction message exclusively as an image representation.

7. The system according to claim 1, including a configuration processor enabling a user to enter data determining a user preference for display of transaction message data exclusively as at least one of, (a) a Hex representation, (b) a non-Hex representation, (c) a binary representation and (d) an image representation.

8. The system according to claim 7, wherein said configuration processor enables a user to enter data determining user preferences for display of different types of transaction message data in corresponding different types of data representations.

9. A system for adaptively displaying transaction message data for use with a data exchange system used for exchanging data between different computer systems using different data formats, comprising:
   a repository of data comprising transaction messages communicated between different computer systems using different data formats;
   a configuration processor enabling a user to enter data determining a user preference for display of transaction message data exclusively as at least one of, (a) a Hex representation, (b) a non-Hex representation, (c) a binary representation and (d) an image representation, said configuration processor enables a user to enter data determining user preferences for display of different types of transaction message data in corresponding different types of data representations;
   a data converter for converting transaction message data derived from the repository into Hex and non-Hex representations;
   a detector for automatically detecting a transaction message type in response to metadata associated with a message; and
   a display processor for providing data representing a first display image including data representing a single transaction message in both Hex and non-Hex data format and enabling a user to initiate generation of a second display image for presenting said transaction message exclusively in a non-Hex representation, said display processor automatically adaptively provides data representing a display image including data representing a single transaction message exclusively in a selected one of Hex, non-Hex and an image representation data format in response to said metadata.

10. A system for adaptively displaying transaction message data for use with a data exchange system used for exchanging data between different computer systems using different data formats, comprising:

a repository of data comprising transaction messages communicated between different computer systems using different data formats;

a configuration processor enabling a user to enter data determining a user preference for display of transaction message data exclusively as at least one of, (a) a Hex representation, (b) a non-Hex representation, (c) a binary representation and (d) an image representation, said configuration processor enables a user to enter data determining user preferences for display of different types of transaction message data in corresponding different types of data representations;

a data converter for converting transaction message data derived from the repository into Hex and non-Hex representations;

a detector for automatically detecting a transaction message type in response to metadata associated with a message; and a display processor for providing data representing a first display image including data representing a single transaction message in both Hex and non-Hex data format and enabling a user to initiate generation of a second display image for presenting said transaction message exclusively in a non-Hex representation, said display processor provides data representing a display image including data representing a single transaction message in a data representation determined in response to said user preferences.

11. The system according to claim 1, wherein said non-Hex representation is an image representation format.

12. The system according to claim 11, wherein said image representation format comprises Binary data.

13. The system according to claim 1, including a data converter for converting transaction message data into an image representation; and a display processor for providing data representing a first display image including data representing a single transaction message in both Hex and non-Hex data format and enabling a user to initiate generation of a second display image for presenting said transaction message exclusively in an image representation format.

14. A system for adaptively displaying transaction message data for use with a data exchange system used for exchanging data between different computer systems using different data formats, comprising:

a repository of data comprising transaction messages communicated between different computer systems using different data formats;

a configuration processor enabling a user to enter data determining user preferences for display of different types of transaction message data in corresponding different types of data representations;

a data converter for converting transaction message data derived from the repository into Hex, non-Hex and image representations;

a detector for automatically detecting a transaction message type in response to metadata associated with a message; and a display processor for adaptively providing data representing a display image including data representing a single transaction message exclusively in a selected one of Hex, non-Hex and an image representation data format in response to user selection of a displayed image element, said display processor automatically adaptively provides data representing a display image including data representing a single transaction message in a selected one of Hex, non-Hex and an image representation data format in response to said metadata.

15. A system for adaptively displaying transaction message data for use with a data exchange system used for exchanging data between different computer systems using different data formats, comprising:

a repository of data comprising transaction messages communicated between different computer systems using different data formats;

a configuration processor enabling a user to enter data determining user preferences for display of different types of transaction message data in corresponding different types of data representations;

a data converter for converting transaction message data derived from the repository into Hex, non-Hex and image representations;

a detector for automatically detecting a transaction message type in response to metadata associated with a message; and a display processor for automatically adaptively providing data representing a display image including data representing a single transaction message exclusively in a selected one of Hex, non-Hex and an image representation data format in response to data indicating predetermined user preferences, said display processor automatically adaptively provides data representing a display image including data representing a single transaction message in a selected one of Hex, non-Hex and an image representation data format in response to said metadata.

16. The system according to claim 15, including a configuration processor enabling a user to enter data determining a user preference for display of transaction message data exclusively as at least one of, (a) a Hex representation, (b) a non-Hex representation, (c) a binary representation and (d) an image representation.

17. The system according to claim 16, wherein said configuration processor enables a user to enter data determining user preferences for display of different types of transaction message data in corresponding different types of data representations.

* * * * *